United States Patent
Tetart et al.

(10) Patent No.: US 10,144,912 B2
(45) Date of Patent: Dec. 4, 2018

(54) USE OF POLYMER FILM FOR PACKAGING A CULTURE MEDIUM

(71) Applicant: BIOMERIEUX, Marcy l'Etoile (FR)

(72) Inventors: Bruno Tetart, Craponne (FR); Nathalie Simon, Grézieu la Varenne (FR)

(73) Assignee: BIOMERIEUX, Marcy l'Etoile (FR)

( * ) Notice: Subject to any disclaimer, the term of this patent is extended or adjusted under 35 U.S.C. 154(b) by 101 days.

(21) Appl. No.: 15/103,135

(22) PCT Filed: Dec. 19, 2014

(86) PCT No.: PCT/FR2014/053461
§ 371 (c)(1),
(2) Date: Jun. 9, 2016

(87) PCT Pub. No.: WO2015/092325
PCT Pub. Date: Jun. 25, 2015

(65) Prior Publication Data
US 2016/0355778 A1  Dec. 8, 2016

(30) Foreign Application Priority Data
Dec. 20, 2013 (FR) ..................... 13 63241

(51) Int. Cl.
| | | |
|---|---|---|
| *C12N 1/00* | (2006.01) | |
| *C12N 1/04* | (2006.01) | |
| *B32B 23/08* | (2006.01) | |
| *B65D 77/04* | (2006.01) | |
| *B65D 65/42* | (2006.01) | |
| *B65B 11/48* | (2006.01) | |
| *B65B 11/50* | (2006.01) | |
| *B65B 55/08* | (2006.01) | |
| *B32B 3/26* | (2006.01) | |
| *B32B 27/30* | (2006.01) | |

(52) U.S. Cl.
CPC ............ *C12N 1/00* (2013.01); *B32B 3/266* (2013.01); *B32B 23/08* (2013.01); *B32B 27/302* (2013.01); *B65B 11/48* (2013.01); *B65B 11/50* (2013.01); *B65B 55/08* (2013.01); *B65D 65/42* (2013.01); *B65D 77/04* (2013.01); *C12N 1/04* (2013.01); *B32B 2307/726* (2013.01); *B65B 2220/20* (2013.01)

(58) Field of Classification Search
None
See application file for complete search history.

(56) References Cited

U.S. PATENT DOCUMENTS 6,491,993 B1 * 12/2002 Forbes ............... B01J 20/28016
428/34.3
2010/0011708 A1   1/2010 Alloin et al.

FOREIGN PATENT DOCUMENTS

| FR | 2913021 A1 | 8/2008 |
| JP | H06-98675 A | 4/1994 |

OTHER PUBLICATIONS

Mar. 18, 2015 Search Report issued in International Patent Application No. PCT/FR2014/053461.
Mar. 18, 2015 Written Opinion issued in International Patent Application No. PCT/FR2014/053461.

* cited by examiner

Primary Examiner — Sheeba Ahmed
(74) Attorney, Agent, or Firm — Oliff PLC

(57) ABSTRACT

A polymer film for packaging at least one microorganism culture medium includes at least one layer of polystyrene and at least one heat-sealing layer. The polymer film has an average water vapor permeability of between 30.0 $g/m^2 \times 24$ hours and 140.0 $g/m^2 \times 24$ hours, preferentially between 70.0 $g/m^2 \times 24$ hours and 120.0 $g/m^2 \times 24$ hours.

23 Claims, 1 Drawing Sheet

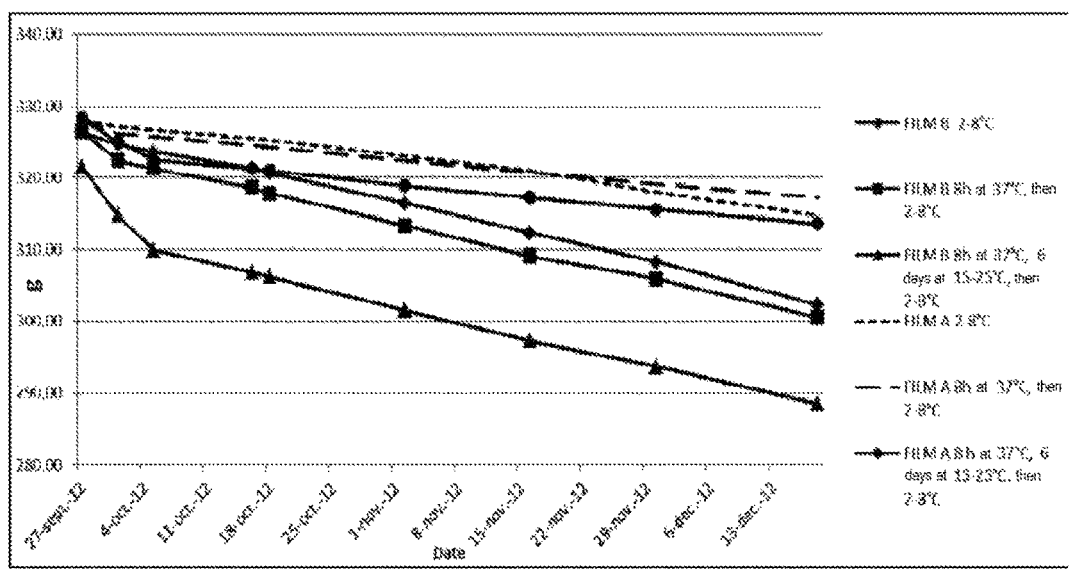

USE OF POLYMER FILM FOR PACKAGING A CULTURE MEDIUM

Many polymer films, capable of being used for packaging products, are present on the market. Mention may in particular be made of films for food-related used, such as polyamide (PA), polyethylene terephthalate (PET) or polyvinyl chloride (PVC) films.

When interest is shown more particularly in the field of in vitro diagnosis, which is the applicant's field of activity, and in particular in films used for bagging culture media, it is noted that the materials normally used are materials which have a low barrier property characterized by a high permeability to water vapour (>120 g/m$^2$×24 hours). Such a material is for example cellophane. This material has the advantage of allowing the water contained in the ready-to-use agar culture media to evaporate and to pass through the film. This then prevents excessive condensation inside the bag consisting of the cellophane film. Conversely, the main drawback is that, since water vapour passes through the film, the moisture content inside is very low, leading to greater and therefore premature drying out of the culture medium. The shelf life of the product is therefore affected by this.

Other materials also used for bagging culture media have, for their part, a high barrier property characterized by a low permeability to water vapour (<5 g/m$^2$×24 hours). This low permeability to water vapour does not make it possible to evacuate the considerable condensation which forms in dishes of ready-to-use agar media, in particular after the media have been poured. It follows that this water remains in the bag until the latter is opened by the final user, generating spots and stains, which is totally unacceptable. Such products are, for example, polyolefins, such as polypropylenes (PPs) or polyethylene (PE). Polyolefins are widely used as packaging material. However, the processes for obtaining such materials mean that the latter have a very low permeability to water vapour. Moreover, materials comprising two complexed films, such as PA+PE films, intended to accentuate their water-vapour-barrier property, are also found. Thus, materials of this type have water-vapour-permeability values lower than about ten grams/m$^2$×24 hours. Known solutions for limiting the amount of water remaining in the bag until opened consists of the use of desiccants such as silica gels in the form of sachets. However, such a method makes it necessary to add an amount of desiccant to each of the bags, thus leading to increased manufacturing costs and a considerable amount of waste.

Finally, other materials also used for bagging culture media comprise a monolayer consisting only of non-oriented PA of "cast" type, and furthermore an amount of PVC and/or polyvinylidene chloride (PVDC) used as basic consistent of a film-sealing coating layer. The advantage of this technique is to be able to modulate the water vapour permeability by varying the amount of coating deposited on the PA film. Materials of this type have a water vapour permeability of between 35 g/m$^2$×24 hours and 110 g/m$^2$×24 hours. However, the processes for producing these films do not make it possible to control the amount of coating deposited on the surface of the film. As a result, the film obtained has a water vapour permeability range which is very variable for the same manufacturing batch. Consequently, the use of this type of film for producing culture media packaging does not make it possible to guarantee a precise shelf life.

It follows that companies which produce agar culture media are still waiting for packaging capable of preserving said culture media, under optimal conditions, mainly in an environment sufficiently rich in water vapour to prevent them from drying out prematurely, but also sufficiently low in water vapour to prevent excessive condensation in the bag, in particular at ambient temperature, in a manner which is predictable and is not very variable over time. Such films should make it possible to limit the agar weight loss kinetics and also the risk of dehydration of the culture media without degrading the level of exudation of the packaging. These properties must, moreover, be combined with a visual rendering in accordance with customer expectations, in particular in terms of transparency, and also a satisfactory resistance to stretching.

It is to the inventors' credit to have demonstrated that it is possible to use, for the purposes of packaging microorganism culture media, films comprising at least one layer of polystyrene and at least one heat-sealing layer and having an average water vapour permeability of between 30.0 g/m$^2$×24 hours and 140.0 g/m$^2$×24 hours, preferentially between 30.0 g/m$^2$×24 hours and 130.0 g/m$^2$×24 hours, more preferentially between 30.0 g/m$^2$24 hours and 120.0 g/m$^2$×24 hours, even more preferentially between 70.0 g/m$^2$×24 hours and 120.0 g/m$^2$×24 hours. The use of these particular materials allows better control of the shelf life, whatever the storage and transportation conditions, storage and transportation at ambient temperature being possible.

Thus, a first objective of the present invention is to provide a use of a film having physical properties, particularly in terms of water-vapour-barrier capacity, capable of allowing an improved and less variable shelf life of microorganism culture media under an atmosphere with a controlled moisture content.

A second objective of the present invention is to provide a use of a film making it possible to reduce the amount of agar present in the microorganism culture medium.

A third objective of the present invention is to provide a use of a thin flexible film having, moreover, a limited cost price.

A fourth objective of the present invention is to provide a use of an easily sealable film for producing a packaging sachet for microorganism culture media.

A fifth objective of the present invention is to provide a use of a film capable of meeting standards in terms of aesthetic appearance, particularly in terms of transparency and feel.

A sixth objective of the present invention is to provide a use of a film capable of meeting standards in terms of tensile strength and of elastic deformation.

A seventh objective of the present invention is to provide a use of a film having physical properties, in particular in terms of water-vapour-barrier capacity, capable of allowing an improved shelf life whatever the temperature conditions.

An eight objective of the present invention is to provide a use of a film having physical properties, particularly in terms of water-vapour-barrier capacity, capable of allowing a decrease in the agar weight loss kinetics and capable of allowing a better stability of the agar weight loss kinetics over time, whatever the temperature conditions.

Another objective of the present invention is to provide a use of a film allowing the production of a reusable and/or recloseable packaging.

These objectives, among others, are achieved by the present invention which relates firstly to the use of a polymer film for packaging at least one microorganism culture medium, said film comprising at least one layer of polystyrene and at least one heat-sealing layer, said film having an average water vapour permeability of between 30.0 g/m$^2$×24 hours and 140.0 g/m$^2$×24 hours, preferentially between 30.0 g/m$^2$×24 hours and 130.0 g/m$^2$×24 hours, more preferentially between 30.0 g/m²×24 hours and 120.0 g/m²×24 hours, even more preferentially between 70.0 g/m²×24 hours and 120.0 g/m²×24 hours.

Alternatively, said film has an average water vapour permeability of between 70.0 g/m²×24 hours and 140.0 g/m²×24 hours, preferentially between 70.0 g/m²×24 hours and 130.0 g/m²×24 hours.

The term "polymer film" is intended to mean a material comprising at least one layer of a polymer material, without size limitation, such as polystyrene. Such films can be produced by extrusion or coextrusion in order to obtain a film comprising several layers, each having their own qualities.

The various measurements of water vapour permeability of the polymer films described in the present invention are determined at 38° C. and 90% relative humidity according to standard NF ISO 2528 (09/2001).

The term "culture medium" is intended to mean a medium comprising all the constituents required for the survival and/or growth of microorganisms, deposited on a support. In practice, those skilled in the art will choose the culture medium as a function of the target microorganisms, according to criteria that are completely known and within the scope of those skilled in the art. A culture medium may be in dehydrated or agar form. In the case of the agar form, the culture medium is contained in a Petri dish. Petri dishes generally consist of a base, into which the agar culture medium, also called agar, is poured while hot, and a lid. The external parts of the base and of the lid cooperate in order to be able to stack several Petri dishes. Generally, stacks of ten dishes are produced for packaging and transportation.

The term "heat-sealing layer" is intended to mean a polymer layer capable of at least partially securing, under the effect of heat, two superimposed edges on at least one side of a film. Preferentially, the securing step is carried out by heat-sealing at a temperature of between 100 and 170° C. Examples of materials that can constitute such a layer are polyethylene, polypropylene or as polyvinyl chloride.

One advantage of the use of a polymer film for packaging at least one microorganism culture medium, comprising at least one polystyrene layer and at least one heat-sealing layer is that of obtaining a reusable and/or recloseable packaging for culture medium, said packaging being non-stretchable. Contrary to the use of particularly ductile, stretchable films such as polyvinyl chloride films, the packaging thus formed by heat sealing can continue to contain or maintain one or more culture media once open. An operator can thus easily move the packaging and its content without risk of causing one or more culture media to fall. Stretchable films are known to tear when opening the packaging, thus preventing any subsequent handling thereof. Furthermore, there is a risk of the media contained by this type of packaging no longer being suitably maintained in a stack after opening.

Advantageously, the film used according to the invention is a non-stretchable film. More advantageously, the heat-sealing layer of the film is non-stretchable in order to make the film used according to the invention non-stretchable.

Preferentially, the film used has an elongation at break of less than 250%, whatever the direction of measurement (machine or transverse direction), allowing it to be not very ductile. More preferentially, the film used has an elongation at break of less than 100%, whatever the direction of measurement (machine or transverse direction), allowing it to be not very ductile at all. Even more preferentially, the film used has an elongation at break of less than 50%, whatever the direction of measurement (machine or transverse direction) in order to ensure better maintaining of the culture media in the packaging after opening.

Preferentially, the film used has a minimal tearing strength of 5 N/mm (ISO 6383-1), whatever the direction of measurement (machine or transverse direction). More preferentially, the film used has a minimal tensile strength of 20 N/mm (ISO 6383-1), according to the direction of machine measurement, allowing it to be stronger.

Preferentially, the film used has a minimal tensile strength of 25 Mpa (ISO 527), whatever the direction of measurement (machine or transverse direction) in order to be sufficiently strong in conventional use.

According to one preferential characteristic, the film used for packaging at least one microorganism culture medium is transparent. This transparency makes it possible in particular to identify by any means the culture medium packaged without opening it. This transparency makes it possible in particular to recognize a bar code present on the culture medium support using a bar code reader or any other imaging means. Another advantage is also that of being able to see the good quality of the culture medium while searching for any defects in appearance and/or contaminations of the culture medium before opening the packaging.

According to another preferential characteristic, the film used for packaging at least one microorganism culture medium comprises at least one microperforated layer.

The "microperforated" is intended to mean any means capable of modifying the water vapour permeability of a polymer layer by producing perforations having sizes of between 10 μm and 50 μm. The number and the spacing of the perforations also make it possible to modify the water vapour permeability of a polymer layer in a controlled manner. Preferentially, the microperforations are produced by a laser. More preferentially, a single layer of polyethylene terephthalate is microperforated. Even more preferentially and in the case where the film comprises two layers of polyethylene terephthalate, these two layers are microperforated.

According to another preferential characteristic, the film used for packaging at least one microorganism culture medium has a thickness of between 20 and 80 μm, preferentially between 30 and 50 μm. A thickness of between 20 and 80 μm makes it possible to guarantee resistance to tearing and an acceptable visual appearance, allowing the operator to easily visualize the type of culture medium packaged in the sachet formed by the film. A thickness of between 30 and 50 μm makes it possible to limit the purchase cost and the use of material while guaranteeing an acceptable visual appearance, it being possible for the thickness range to be adjusted to the appearance of the culture medium packaged and to the desired resistance to tearing.

Another subject of the invention relates to the use of a polymer film as described above, for producing a sachet intended for the packaging of at least one microorganism culture medium.

Another subject of the invention relates to a process for packaging at least one culture medium, comprising the steps consisting in:
  placing the culture medium or media on a film as described above, on the heat-sealing layer of said film;
  covering the culture medium or media with a portion, which has remained free, of said film or with another film, such that the heat-sealing layers are facing one another;
  securing the edges of the film or of the two films, such that the culture medium or media is or are trapped in the sachet thus formed.

Preferentially, the film(s) is (are) presterilized. The sterilization method may be irradiation with radiation taken from the group consisting of gamma-rays and/or beta-rays.

Preferentially, the securing step is a heat-sealing step at a temperature of between 100 and 170° C.

According to another preferential characteristic, the packaging process according to the invention also comprises the additional steps consisting in:
placing the sachet thus obtained inside a second sachet and
sealing said second sachet.

According to another preferential characteristic, the packaging process according to the invention also comprises the additional steps consisting in:
placing the second sachet thus obtained inside a third sachet and
sealing said third sachet.

According to another preferential characteristic, said second and/or third sachets of the packaging process according to the invention consist of a material taken from the group comprising: cellophane, polyolefins and polyamides.

According to another preferential characteristic, said second and/or third sachets of the packaging process according to the invention consist of a film comprising at least one layer of polystyrene and at least one heat-sealing layer, such as polyethylene, said film having an average water vapour permeability of between 30.0 g/m²×24 hours and 140.0 g/m²×24 hours, preferentially between 30.0 g/m²×24 hours and 130.0 g/m²×24 hours, more preferentially between 30.0 g/m²×24 hours and 120.0 g/m²×24 hours, even more preferentially between 70.0 g/m²×24 hours and 120.0 g/m²×24 hours.

Alternatively, said second and/or third sachets of the packaging process according to the invention consist of a film having an average water vapour permeability of between 70.0 g/m²×24 hours and 140.0 g/m²×24 hours, preferentially between 70.0 g/m²×24 hours, preferentially between 70.0 g/m² and 130.0 g/m²×24 hours.

Another subject of invention also relates to the use of a film as described above for packaging at least one culture medium in an isolator or in a laminar air flow hood. The advantage of the use of such a film in this type of application is that of being able to decontaminate the outside of a packaging formed by a said film without risk of damaging the culture medium or media present in the packaging or of destroying any microorganisms present on the culture medium for analysis. Indeed, such a film is impermeable to the principal decontaminating gases used in isolators, such as hydrogen peroxide ($H_2O_2$) or peracetic acid ($C_2H_4O_3$).

The objectives and advantages of the present invention will be understood more clearly on reading the following examples, which are in no way limiting, with reference to the drawing.

FIG. 1 shows the measurements of the weights of the complete stacks of dishes week by week for batches BATCH 1 and BATCH 2 as a function of the storage temperatures.

EXAMPLE

Various batches of Petri dishes are formed. Each of the batches contains ten agar culture media of Mac Conkey type, manufactured by the applicant.

The first batch, BATCH 1, comprises three stacks of ten Petri dishes, each stack being packaged in a sachet made from a PS film comprising a layer of polystyrene, called FILM A, having a thickness of 30 μm.

The second batch, BATCH 2, comprises three stacks of ten Petri dishes, each stack being packaged in a sachet made from a reference film comprising a layer of cellophane, called FILM B, having a thickness of 30 μm and a water vapour permeability of approximately 370 g/m²×24 h.

The water vapour transmission coefficient of film A is determined by five measurements according to the above-mentioned standard. The results are indicated in Table 1a below.

TABLE 1a

| | Water vapour transmission coefficient | | | | | |
| | (g/m².24 h) | | | | | |
| Reference | Results | | | | Mean | Standard Deviation |
|---|---|---|---|---|---|---|
| FILM A: PS | 97.3 | 97.3 | 97.2 | 99.4 | 95.7 | 97.4 | 1.3 |

The mechanical characteristics of FILM A are indicated in table 1b below:

TABLE 1b (MD: machine direction, TD: transverse direction).
The values in this table obey a tolerance of 20%.

| Characteristics | Methods | Values | Units |
|---|---|---|---|
| Thickness | NFT 54-101 | 30 | μm |
| Corona treatment | | if necessary | |
| Density | ISO 1183 | 1.036 | |
| Tensile strength | ISO 527 | MD: 34 TD: 30 | Mpa |
| Elongation at break | ISO 527 | MD: 6 TD: 5 | % |
| Tearing strength | ISO 6383-1 | MD: 20 TD: 5 | N/mm |
| Impact strength | ISO 7765-1 | <25 - method A | g |

Each of the three stacks of the two batches thus formed is then stored for 11 weeks according to several temperature conditions. A first stack of each batch is thus stored at a temperature of between 2 and 8° C. A second stack of each batch is stored for 8 hours at 37° C., then at a temperature of between 2 and 8° C. A third stack of each batch is stored for 8 hours at 37° C., then for 6 days at a temperature of between 15° C. and 25° C. and finally at a temperature of between 2 and 8° C.

The total weight of each stack of each batch is measured every week in order to determine the agar weight loss kinetics as a function of the storage and packaging conditions. The monitoring of the weight of the agar is an indicator for the amount of water lost by the agar.

The results of these measurements are given in the table below and in relation to FIG. 1.

Table 2 shows the monitoring of the weight, in grams, of the stacks of dishes, for each batch.

TABLE 2

| | 27 Sep. 2012 | 1 Oct. 2012 | 5 Oct. 2012 | 16 Oct. 2012 | 18 Oct. 2012 | 2 Nov. 2012 | 16 Nov. 2012 | 30 Nov. 2012 | 18 Dec. 2012 |
|---|---|---|---|---|---|---|---|---|---|
| FILM B 2-8° C. | | 326.44 | 324.68 | 323.63 | 321.32 | 320.64 | 316.45 | 312.26 | 308.21 | 302.28 |
| FILM B 8 h at 37° C., then 2-8° C. | | 326.49 | 322.38 | 321.28 | 318.60 | 317.82 | 313.29 | 309.04 | 305.84 | 300.46 |
| FILM B 8 h at 37° C., 6 days at 15-25° C., then 2-8° C. | | 321.59 | 314.70 | 309.90 | 306.78 | 306.16 | 301.48 | 297.24 | 293.64 | 288.50 |
| FILM A 2-8° C. | | 327.84 | 327.17 | 326.66 | 325.50 | 325.22 | 322.98 | 321.01 | 318.00 | 314.73 |
| FILM A 8 h at 37° C., then 2-8° C. | | 328.14 | 326.16 | 325.73 | 324.52 | 324.25 | 322.34 | 320.78 | 319.06 | 317.26 |
| FILM A 8 h at 37° C., 6 days at 15-25° C., then 2-8° C. | | 328.32 | 324.97 | 322.52 | 321.28 | 321.02 | 318.90 | 317.23 | 315.52 | 313.57 |

Table 2 and FIG. 1 thus show a reduction in the agar weight loss kinetics due to the use of the films FILM A in comparison with a reference film FILM B.

The results regarding the agar weight loss kinetics were obtained while maintaining an acceptable level of condensation inside the sachets using FILM A, contrary to the sachets using standard plastic films.

A decrease in the agar weight loss kinetics is demonstrated whatever the storage conditions. The influence of the temperature on the agar weight loss kinetics is decreased due to the use of FILM A in comparison with the reference film FILM B used to produce the sachets. Indeed, all storage conditions taken into account, the agar weight loss is decreased for the batch using films FILM A. The stacks of batches stored at a temperature of between 2 and 8° C. in films FILM A exhibit in particular a slight decrease in weight as the weeks go by, in comparison with the stacks packaged in films FILM B. The improvement is even more notable for the stacks stored for 8 hours at 37° C., then for 6 days at a temperature of between 15° C. and 25° C. and finally at a temperature of between 2 and 8° C.

Finally, better stability of the agar weight loss kinetics is also demonstrated, whatever the storage conditions, the measurements carried out on batches packaged by FILM B showing a greater variation in the agar weight loss kinetics over time.

These results thus make it possible to envisage a reduction in the amount of agar able to be poured into a Petri dish, nevertheless making it possible to ensure a shelf life in keeping with current standards. Conversely, extended shelf lives can be achieved using films according to the invention by retaining a similar amount of poured agar. The use of a film according to the invention therefore allows a reduction in the manufacturing costs and/or an extension of the shelf life of the culture media.

The invention claimed is:

1. A polymer film for packaging at least one microorganism culture medium, said film comprising at least one layer of polystyrene and at least one heat-sealing layer, wherein at least one of the layers is microperforated so as to include perforations having sizes of between 10 µm and 50 µm and the film has an average water vapour permeability of between 30.0 g/m²×24 hours and 140.0 g/m²×24 hours.

2. The polymer film according to claim 1, wherein the film has a thickness of between 20 and 80 µm.

3. A sachet containing at least one microorganism culture medium that are each deposited on a separate support, wherein the sachet is produced from the polymer film according to claim 1.

4. A process for packaging at least one microorganism culture medium, comprising:
   placing the culture medium or media on the heat-sealing layer of the polymer film according to claim 1;
   covering the culture medium or media with a portion, which has remained free, of said film or with another film, such that the heat-sealing layers are facing one another; and
   securing the edges of the film or of the two films, such that the culture medium or media is or are trapped in a sachet thus formed.

5. The packaging process according to claim 4, wherein the film(s) is (are) presterilized.

6. The packaging process according to claim 5, wherein the sterilization method is irradiation with radiation selected from the group consisting of gamma-rays and beta-rays.

7. The packaging process according to claim 4, wherein the securing step is a heat-sealing step at a temperature of between 100 and 170° C.

8. The packaging process according to claim 4, further comprising:
   placing the sachet inside a second sachet; and
   sealing said second sachet.

9. The packaging process according to claim 8, further comprising:
   placing the second sachet inside a third sachet; and
   sealing said third sachet.

10. The packaging process according to claim 9, wherein said second and/or third sachets are made from a material selected from the group consisting of cellophane, polyolefins and polyamides.

11. The polymer film according to claim 1, wherein the heat-sealing layer is a polyethylene, polypropylene, or polyvinyl chloride layer.

12. The packaging process according to claim 4, wherein each culture medium trapped in the sachet is deposited on a separate support.

13. A polymer film for packaging at least one microorganism culture medium, said film comprising at least one layer of polystyrene and at least one heat-sealing layer, wherein the film has a thickness of between 20 and 80 µm and an average water vapour permeability of between 30.0 g/m²×24 hours and 140.0 g/m²×24 hours.

14. A sachet containing at least one microorganism culture medium that are each deposited on a separate support, wherein the sachet is produced from the polymer film according to claim 13.

15. A process for packaging at least one microorganism culture medium, comprising:
    placing the culture medium or media on the heat-sealing layer of the polymer film according to claim 13;
    covering the culture medium or media with a portion, which has remained free, of said film or with another film, such that the heat-sealing layers are facing one another; and
    securing the edges of the film or of the two films, such that the culture medium or media is or are trapped in a sachet thus formed.

16. The packaging process according to claim 15, wherein the film(s) is (are) presterilized.

17. The packaging process according to claim 16, wherein the sterilization method is irradiation with radiation selected from the group consisting of gamma-rays and beta-rays.

18. The packaging process according to claim 15, wherein the securing step is a heat-sealing step at a temperature of between 100 and 170° C.

19. The packaging process according to claim 15, further comprising:
    placing the sachet inside a second sachet; and
    sealing said second sachet.

20. The packaging process according to claim 19, further comprising:
    placing the second sachet inside a third sachet; and
    sealing said third sachet.

21. The packaging process according to claim 20, wherein said second and/or third sachets are made from a material selected from the group consisting of cellophane, polyolefins and polyamides.

22. The polymer film according to claim 13, wherein the heat-sealing layer is a polyethylene, polypropylene, or polyvinyl chloride layer.

23. The packaging process according to claim 15, wherein each culture medium trapped in the sachet is deposited on a separate support.

* * * * *